US012573492B2

(12) United States Patent
Lefebvre et al.

(10) Patent No.: US 12,573,492 B2
(45) Date of Patent: Mar. 10, 2026

(54) METHOD FOR EVALUATING THE BODY ACTIVITY OF A USER

(71) Applicant: ORANGE, Issy-les-Moulineaux (FR)

(72) Inventors: Grégoire Lefebvre, Chatillon Cedex (FR); Paul Compagnon, Chatillon Cedex (FR)

(73) Assignee: ORANGE, Issy-les-Moulineaux (FR)

( * ) Notice: Subject to any disclaimer, the term of this patent is extended or adjusted under 35 U.S.C. 154(b) by 496 days.

(21) Appl. No.: 17/299,581

(22) PCT Filed: Oct. 30, 2019

(86) PCT No.: PCT/FR2019/052575
§ 371 (c)(1),
(2) Date: Jun. 3, 2021

(87) PCT Pub. No.: WO2020/115377
PCT Pub. Date: Jun. 11, 2020

(65) Prior Publication Data
US 2022/0059207 A1      Feb. 24, 2022

(30) Foreign Application Priority Data

Dec. 4, 2018      (FR) ...................................... 1872281

(51) Int. Cl.
*G16H 20/30*        (2018.01)
*G06F 16/28*        (2019.01)
(52) U.S. Cl.
CPC ........... *G16H 20/30* (2018.01); *G06F 16/285* (2019.01)

(58) Field of Classification Search
CPC ..... G16H 20/30; G06F 16/285; G06F 16/906; A61B 5/0022; A61B 5/1116; A61B 5/1118; A61B 5/7264; A61B 5/746
See application file for complete search history.

(56) References Cited

U.S. PATENT DOCUMENTS 10,055,549 B2 * 8/2018 Chung ................... G16H 50/20
2007/0225935 A1 9/2007 Ronkainen et al.
(Continued)

FOREIGN PATENT DOCUMENTS

EP        3131366 A1      2/2017

OTHER PUBLICATIONS

Sprint, G.; Cook, D.; Weeks, D.; Dahmen, J.; La Fleur, A. Analyzing Sensor-Based Time Series Data to Track Changes in Physical Activity during Inpatient Rehabilitation. Sensors 2017, 17, 2219. https://doi.org/10.3390/s17102219 (Year: 2017).*
(Continued)

*Primary Examiner* — Eliza A Lam
(74) *Attorney, Agent, or Firm* — David D. Brush; Westman, Champlin & Koehler, P.A.

(57) ABSTRACT
A method of evaluating the body activity of a user includes: at a given date and for a given duration, acquiring movement data from the user, distributing the acquired movement data corresponding to different types of movement, calculating a data structure representative of the body activity of the user performed at the given date and for the given duration, comparing the data structure with at least one other structure representative of the body activity performed at a date prior to the given date and for the given duration, duplicating the comparisons for different durations and determining an objective measurement of the user's autonomy.

6 Claims, 7 Drawing Sheets

(56) References Cited

U.S. PATENT DOCUMENTS

| | | |
|---|---|---|
| 2014/0279740 A1 | 9/2014 | Wernevi et al. |
| 2016/0038061 A1 | 2/2016 | Kechichian et al. |
| 2016/0262687 A1* | 9/2016 | Vaidyanathan ...... A61B 5/0205 |
| 2017/0011210 A1 | 1/2017 | Cheong et al. |
| 2017/0032692 A1* | 2/2017 | Choi ...................... H04W 4/02 |
| 2017/0080288 A1* | 3/2017 | Roh ..................... A61B 5/6898 |
| 2019/0038179 A1* | 2/2019 | Tanriover ............. A61B 5/0803 |

OTHER PUBLICATIONS

International Search Report dated Jan. 27, 2020 for corresponding International Application No. PCT/FR2019/052575, Oct. 30, 2019.
Written Opinion of the International Searching Authority dated Jan. 27, 2020 for corresponding International Application No. PCT/FR2019/052575, filed Oct. 30, 2019.
Lawton et al., "Assessment of Older People: Self-Maintaining and Instrumental Activities of Daily Living", The Gerontologist 9, 3 Part 1 (1969), 179-186.
English translation of the Written Opinion of the International Searching Authority dated Jun. 8, 2021 for corresponding International Application No. PCT/FR2019/052575, filed Oct. 30, 2019.

\* cited by examiner

FIGURE 4A                    FIGURE 4B                FIGURE 4C

METHOD FOR EVALUATING THE BODY ACTIVITY OF A USER

CROSS-REFERENCE TO RELATED APPLICATIONS

This Application is a Section 371 National Stage Application of International Application No. PCT/FR2019/052575, filed Oct. 30, 2019, the content of which is incorporated herein by reference in its entirety, and published as WO 2020/115377 on Jun. 11, 2020, not in English.

FIELD OF THE DISCLOSURE

The present invention relates generally to the field of remotely measuring and tracking the body activity of a person.

The invention relates more particularly to remotely measuring and tracking of an indicator of autonomy of frail or isolated persons.

BACKGROUND OF THE DISCLOSURE

Currently, the systems for remotely measuring and tracking the autonomy of a person are executed according to different methods.

According to a first method described in the document "Assessment of Older People: Self-Maintaining and Instrumental Activities of Daily Living", Lawton et al., The Gerontologist 9, 3_Part_1 (1969), 179-186, it involves producing a questionnaire on the various habits of the subject to be evaluated and the subject is asked to complete it. This method can be improved because it entails a risk of the questionnaire not being completed by the subject and requires, in order to remove this risk, a third person (surveyor, auditor, etc.) to be brought in to assist the subject in completing the questionnaire. In addition, this method does not correspond to an objective analysis of autonomy level since the questionnaire is completed by the subject themself.

Other methods use motion detection sensors such as, for example, inertial sensors (experimental equipments, smartphones, connected watches) and/or visual sensors (cameras installed in the measurement location) in order to be able to infer, from the data from these sensors, the motions of the subject. The identified motion data are then classified by types of motions or postures (sitting, standing, lying, walking, running, etc.) and these methods compare the motions of the subject performed in real time with the classified motion data, in order to identify anomalous behaviors and to alert a third party. However, such methods, referred to as supervised methods, require a database of reference motions to be implemented. The data in this database are compared with the data from the sensors, in order to infer therefrom the movement performed by the subject. These methods by supervised analysis of the data do not allow postures to be accurately identified. Specifically, there can be confusion in determining certain postures, such as for example the sitting or standing position detected by an inertial sensor, if the person has the same orientation and the same dynamics. Consequently, these methods by supervised analysis often contain only four different types of posture information (sitting, standing, lying, walking), not allowing reliable alerting. In particular, such methods are liable to trigger false alarms or, conversely, not to trigger an alarm in situations in which assistance is in fact needed.

According to another method described in document US 2014/0279740, to improve and therefore refine the identification of the movements of a subject, it is proposed to use a number of inertial motion sensors arranged at strategic locations on the body (legs, arms, fingers, head) and camera-type image sensors installed in the one or more living spaces. Such an alternative method, although effective in identifying motions, is difficult to realize over long-term tracking of the person because it forces the subject to:
- wear various sensors on their body, which is not compatible with real-time tracking of activity day and night and for long periods,
- be filmed, which may be considered by some subjects to be a protection-related constraint on their private life. This also requires a complex and expensive setup at the home of the person to be monitored.

In order to remotely evaluate the autonomy of a person over a long period, the methods presented above are therefore unsuitable. Indeed, in order to evaluate the autonomy of a person, it is furthermore necessary to have a fairly comprehensive picture of the movements performed, in order to infer the activities specific to this person (for example the activity of getting out of bed which is defined by a series of movements of the type being recumbent, turning, sitting, standing up, walking) and to check at various times whether these activities are repeated (establishing habits) or not.

SUMMARY

One of the aims of the invention is to overcome drawbacks of the aforementioned prior art.

To that end, one subject of the present invention relates to a method for evaluating the body activity of a user, implemented by a computing device, characterized in that it comprises the following:
- on a given date and for a given duration, acquiring data on the motion of said user from a motion sensor,
- distributing said acquired motion data into different data groups corresponding, respectively, to different types of motion,
- on the basis of said data thus distributed, calculating a data structure representative of the body activity of said user that is undertaken on said given date and for said given duration,
- comparing said data structure with at least one other data structure representative of the body activity of said user that was undertaken on a date prior to said given date and for said given duration,
- as a result of said comparison, evaluating a variation between the body activity of the user undertaken on said given date and for said given duration, and the body activity of the user undertaken on at least the prior date and for said given duration.

The acquired motion data are raw data. The term "raw data" is understood to mean data derived essentially from the motions of said user. These data do not integrate additional data such as data from models representative of motions of other users.

Distributing these raw data into different data groups corresponding, respectively, to different types of motion amounts to classifying these raw data in at least one data class, according to at least one non-supervised classification method.

The data class thus represents an anonymized posture of the person.

By virtue of the invention, it is possible to evaluate, almost in real time (for a given period of time), the variations in the activities of a user, by comparing the data structures calculated on the given date and for the given duration with at least one other data structure calculated on a date prior to said given date and for a given duration which is the same as the duration on said given date. Given the acquisition, distribution and calculation operations implemented according to the method described above, the invention therefore makes it possible to detect and classify different motion data by means of non-supervised data classification or analysis techniques. These classification techniques do not aim to characterize and name the motion data in terms of movements, as is performed for example in the prior art, but rather only to group motion data together because they represent a similar movement without, however, characterizing this movement. These non-supervised classification techniques allow non-linear differentiation of the different data on the motions of the person, which makes it possible to accurately distinguish each motion of the user. These non-supervised classification techniques do not require the comparison of the raw data with data models as is the case with supervised classification techniques. Such fine distinction of the different motion raw data makes it possible to measure different body activities of the user and to track their variations over time.

This invention also does not allow the motion raw data to be associated with everyday movements (sitting, standing, lying, walking, etc.), unless complex analyses are performed in order to characterize these movements without guaranteed results. This difficulty in association in fact constitutes an advantage because it strengthens the protection of the personal data of the user.

According to one particular embodiment, said other data structure is selected from among a plurality of data structures representative of the body activity of said user, which were calculated on a date prior to said given date and for said given duration.

By virtue of this embodiment, it is thus possible to compare similar body activities. For example, the current body activity, undertaken in a given timeslot, for example Monday between 08:30 and 09:30, may be compared with the same body activity undertaken on the same day of the week as the given day (Monday), but for example in previous weeks, for example between 08:30 and 09:30 because this corresponds to timeslots for which this user is in the habit of performing the same activities. The assumption is that autonomy is strongly linked to the habits (recurrence of certain body activities in the same or similar timeslots) of a user. It is therefore essential to choose dates wisely in order to compare periods in which the body activities of the user are similar, in order to detect deviations in activities and therefore signs of loss of autonomy of the user. However, the chosen dates do not necessarily have to follow a set periodic rule (every week at the same time) if the habits of the person necessitate choosing dates without apparent logic between them in terms of periodicity. This choice of dates to be compared may be made by the user, a close friend or family member, a practitioner or any other third party aware of the habits of the user.

According to one particular embodiment, said duration is determined with respect to the obtaining of a desired minimum number N of different data groups, into which to distribute the acquired motion data.

By virtue of this other embodiment, choosing overly short durations is avoided, in which case it would not be possible to record enough motion data to compare body activities.

Furthermore, the duration is indexed according to a minimum number N of motion data rather than over a minimum duration in order to take into account the timeslots in which the user is inactive in which substantial lengths of time can pass without any particular activity from the person (sleep for example).

According to one particular embodiment, an autonomy value A is calculated according to a plurality of variation evaluations calculated for a plurality of given durations.

By virtue of this particular embodiment, it is thus possible to estimate an objective value of the autonomy of the user. For this, the method compares the most recent activity of the user in a timeslot in question (for example a whole hour preceding the time of the comparison) with prior activities of the same duration already saved, for example in dedicated databases. It then generalizes this calculation over other timeslots (for example the day, week, month or year preceding the comparison) by comparing the most recent activity compatible with the analysis timeslots with prior activities in the same timeslots (for example, all of the Mondays already recorded for daily timeslots, every week already recorded for weekly timeslots etc.). This generalized comparison of body activity over different periods of the life of a user makes it possible to detect not only changes in habits in well-targeted activities which last of the order of an hour (having lunch, practicing sport, watching a movie, eating, etc.) but also in a plurality of activities which take place over longer periods (days, weeks) to very long periods (months, years). This measurement of changes in habits is closely related to the notion of autonomy, since it is known to a person skilled in the art that an autonomous person lives in a habit-based manner while the changes in habits, and thus loss of references, are signs of the failing autonomy of a person. The method therefore seeks to provide a value of the autonomy, and therefore of the loss of autonomy, of a user which is quantifiable and objective since it is based on measurements and calculated by a machine. This autonomy value allows the person responsible for tracking the user (family, physician, etc.) to be regularly informed of the level of autonomy of the user in order to take actions as deemed necessary.

According to another particular embodiment, to calculate the autonomy value A, each of said variation evaluations is respectively assigned a weighting coefficient.

By virtue of this other embodiment, the weighting of each variation in body activity of the user makes it possible to take into account periods that are more relevant than others in the analysis of changes in habits. Specifically, it is conceivable that the measurement of changes in activity in the preceding days is more significant with respect to a change in autonomy than the same measurement performed longer ago, for example for days of the preceding year. Furthermore, the weighting can also be used to increase the influence of the measurements of variation in body activity in the measurement of autonomy as a function of the duration of the timeslots used for the measurements. Specifically, it is conceivable that the measurement of a variation in activity over a short duration (of the order of an hour), which targets a well-specified activity, may have greater influence than a measurement of variation in activity over a year which represents such a large number of activities that it is no longer truly representative of a value of the autonomy of the user.

According to another particular embodiment, the method comprises the following:
    comparing the autonomy value with a certain value,
    depending on the result of the comparison, generating
        information relating to the calculated variation.

By virtue of this other embodiment, the triggering of the action which indicates the loss of autonomy is dependent on a single parameter of numerical type. It is therefore easy to define a threshold for triggering an action. In the closest prior art, no method allows the triggering of an alert linked to a loss of autonomy.

According to another particular embodiment, the generated information is communicated to a person authorized by said user.

By virtue of this other embodiment, it is possible to inform a third party regarding a potential loss of autonomy of the user. Because of the absence of naming and characterization of the motion raw data transmitted in such information, the action of the type of communicating to a third party does not in fact disclose the body activities of the user to the third party who receives this information and thus protects the confidentiality of the personal data of the user.

The various embodiments or features described above may be added, independently or in combination with one another, to the evaluation method defined above.

The invention also relates to a device for evaluating the body activity of a user, such a device comprising a processor which is configured to implement the following:

on a given date and for a given duration, acquiring data on the motion of said user from a motion sensor, distributing said acquired motion data into different data groups (Sri) corresponding, respectively, to different types of motion, on the basis of said data thus distributed, calculating a data structure representative of the body activity of said user that is undertaken on said given date and for said given duration, comparing said data structure with at least one other data structure representative of the body activity of said user that was undertaken on a date prior to said given date and for said given duration, as a result of said comparison, evaluating a variation between the body activity of the user undertaken on said given date and for said given duration, and the body activity of the user undertaken on at least the prior date and for said given duration.

Such a computing device is, in particular, able to implement the method for evaluating the body activity of a user described above, according to any one of the embodiments described above.

The invention further relates to a computer program comprising instructions for implementing the method for evaluating the body activity of a user, according to any one of the particular embodiments described above, when said program is executed by a processor.

This program may use any programming language, and be in the form of source code, of object code, or of intermediate code between source code and object code, such as in a partially compiled form, or in any other desirable form.

The invention also relates to a computer-readable storage medium or recording medium, comprising instructions of a computer program as mentioned above.

The recording medium may be any entity or device capable of storing the program. For example, the medium may include a storage means, such as a ROM, for example a CD-ROM or a microelectronic circuit ROM, or a magnetic recording means, for example a USB stick or a hard disk.

Furthermore, the recording medium may be a transmissible medium such as an electrical or optical signal, which may be routed via an electrical or optical cable, by radio or by other means. The program according to the invention may in particular be downloaded from an Internet network.

As an alternative, the recording medium may be an integrated circuit within which the program is incorporated, the circuit being designed to execute or to be used in the execution of the evaluation method described above.

BRIEF DESCRIPTION OF THE DRAWINGS

Other features and advantages of the invention will become more clearly apparent from reading the following description of particular embodiments, given by way of merely illustrative and non-limiting examples, and the appended drawings, in which.

DETAILED DESCRIPTION OF ILLUSTRATIVE EMBODIMENTS

General Principle of the Invention

Figure 1:
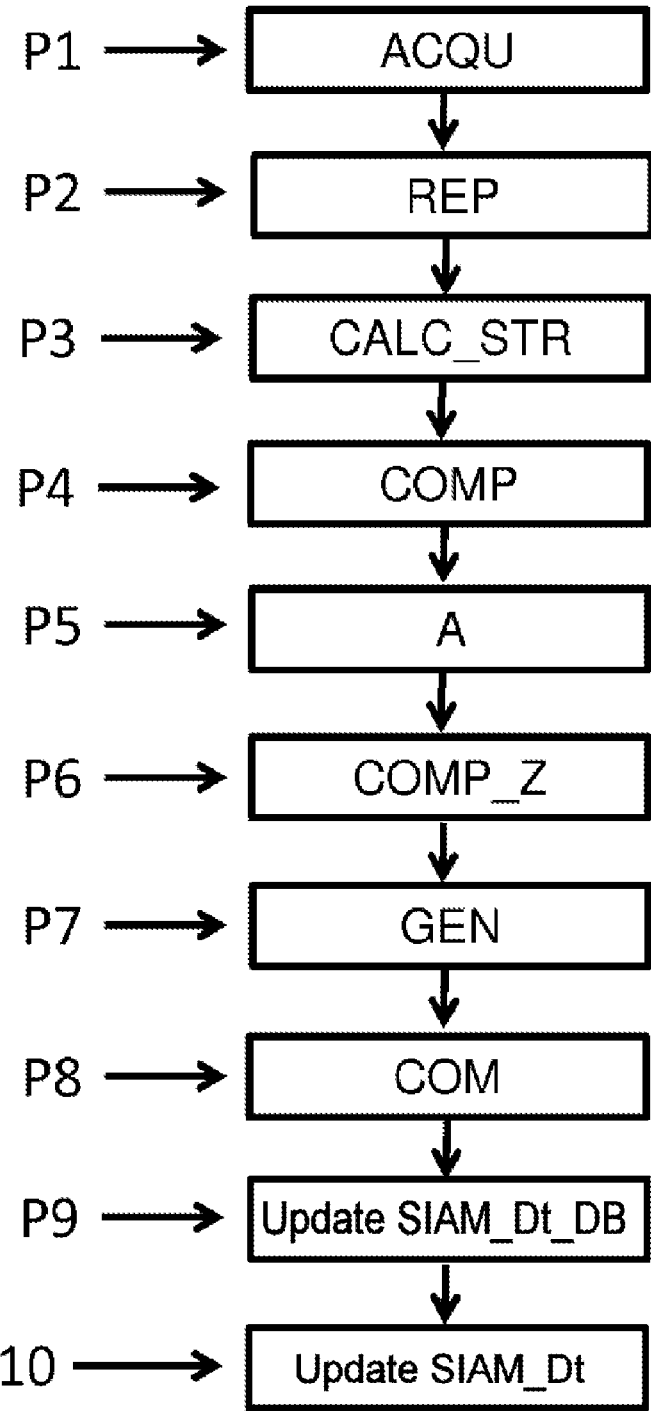
FIG. 1 shows the main actions performed by the method for evaluating the body activity of a user according to one embodiment of the invention.

The objective of this invention is to provide an automatic metric in order to evaluate the body behavior of an individual as being a situational habit or, conversely, a rare event, and to provide a degree of information to whom it may concern by various communication means.

The invention primarily provides a method and a device for calculating a measurement of the autonomy of a person tracked remotely using raw data from one or more motion sensors worn/carried by the person. The objective is not, like a substantial number of solutions of the market, to send alerts on a one-off event (fall, illness, etc.) but rather to provide tracking over time of the body activity of the person in order to inform medical staff, family or any interested third party if there is a change in the habits of the person. Such an autonomy measurement takes, for example, the form of an autonomy index on a scale of 0 to 1:0.1 everything is fine, 0.5 there is cause to worry, 0.9 intervention is urgently needed.

The method works by detecting postures specific to the individual by means of what are called pre-clustering methods (classification of similar raw data into data classes by means of non-supervised methods for clustering by means of non-linear separator) via the analysis of different inertial data streams (accelerometer, gyroscope, magnetometer) from the one or more sensors.

Supervised data analysis methods do not allow postures to be accurately identified, due to possible confusion in determining certain postures, such as for example the sitting or standing position detected by an inertial sensor, if the person has the same orientation and the same dynamics. Additionally, often only four different types of information are used with this type of method (sitting, standing, lying, walking).

The invention proposes bypassing these problems by providing a near-unsupervised model able to isolate postures and to produce groups of postures without necessarily characterizing these postures (sitting, lying, standing, etc.). The postures are therefore anonymized because they cannot be characterized by the method and the method therefore does not allow the postures of said person to be characterized with time. These postures, represented by the data classes in the method, may be many in number and characteristic of the individual. This method, to be effective, requires the use of only one inertial sensor.

Over a predefined duration, the method analyzes and identifies the data classes and creates a data structure, such as, for example, a list, a matrix, a vector, etc. characterizing an aggregate of the data classes over this duration. This data structure is a representation of behaviors or activities such as for example: I get up in the morning, I turn on the coffee maker, I make breakfast, I have breakfast, I brush my teeth, etc.

These sequences of data classes may be analyzed every hour or for different (shorter or longer) durations depending on what it is desired to analyze and also over timespans specifically defined by the model or by an expert, since they represent particular times of the day (breakfast, lunch, afternoon walk, etc.). This analysis is performed in real time in each of the chosen timeslots.

Next, these behavior models are compared with other previously saved models to identify similarities in behaviors at appropriate times. These appropriate times may be the comparison of a timeslot with the same timeslot on each day of the past week or on every Monday of the past weeks. This measurement of similarity is calculated using neural networks (model which has to be trained) and may be performed directly in the terminal incorporating the inertial data sensor (for example a smartphone or a connected watch) or a remote equipment such as a computer or server or a mix of the two equipments.

Thus, it is therefore possible to calculate a variation in body activity on the basis of the weighted average of the similarities in behavior over a plurality of appropriate times chosen for their relevance and having the same duration. This calculation also makes it possible to provide a first estimate of an index of autonomy of the person since it measures the variations in the activity of a user in a timeslot (of the order of an hour for example) with respect to their past activities in the same timeslot. However, for a more accurate estimate, the invention proposes comparing activities over longer analysis durations such as for example over a whole day (from 00:00 to 24:00) or a rolling day (from 08:00 to 08:00 the next day). Even though an analysis with respect to the day is perhaps less relevant, it will give information that will allow the invention to refine the autonomy value. With this in mind, different weights may be given to the comparison of body activities in hourly timeslots or in daily timeslots, etc. In order to further refine the measurement of autonomy, this principle of weighted comparison over different timeslots can be generalized for even longer durations (weeks, months, years) and is limited only by the history of the recordings of the raw data on the motion of the user.

An autonomy value A calculated on completion of the method according to the invention is, according to one possible embodiment, compared with a threshold Z. An alarm is then raised if the value A is higher than the threshold Z. This alarm triggers the transmission of information to a third party, such as for example a member of the family, the personal physician, a service company, a care facility and even any company or entity capable of providing an even partial response to these changes in habit (example: provider of music content, of movies, etc.).

Particular embodiments of the invention.

Described below, with reference to FIGS. 1 to 7, is a method for evaluating the body activity of a user.

Such a method takes place in the following manner.

In FIG. 1, in P1, a raw data sensor CAP continuously records, on a transitory or non-transitory storage medium (shown and referred to as MEM_CAP in FIG. 2), the numerical raw data describing the motion of a user. Such a sensor is for example worn/carried by the user. It is, for example, an accelerometer, gyrometer, magnetometer, etc. commonly installed in a cellular telephone, or any portable device such as a connected object. In one exemplary implementation, the stored raw data are transmitted to an database MVT_DB which is the main knowledge base describing the motions of a person for a long duration of the order of several months to several years (the years 2016, 2017 and some of 2018 in this example).

Figure 2:
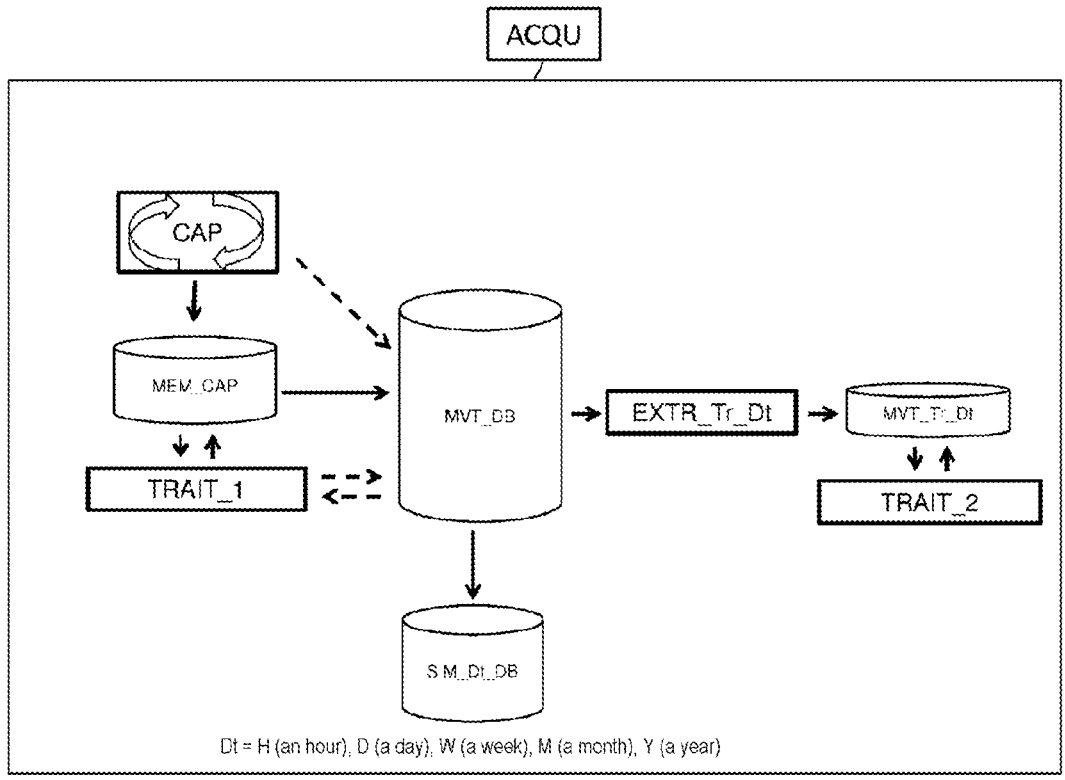
FIG. 2 shows one of the actions performed by the method of FIG. 1 in greater detail.

In one alternative embodiment, as described in FIG. 2, the continuously recorded data ACQU in P1 are either directly transmitted by the sensor and recorded in the database MVT_DB (dashed arrow), or stored in the memory of the sensor MEM_CAP. The set of these collected raw data constitutes a raw database.

This database is then broken down by the method into a plurality of databases SIM_Dt_DB which differ according to the duration of analysis. In this example, SIM_H_DB represents motion raw data for similar timeslots of an hour (10:00-11:00) or dissimilar timeslots (00:00-10:00-12:00-24:00), SIM_D_DB for similar days (all of the Mondays in the database from 2017) and dissimilar days (all of the Tuesdays, Wednesdays, Thursdays, Fridays, Saturdays and Sundays in the database), SIM_W_DB for similar weeks (Week 5 of 2017 and 2018) and dissimilar weeks (the other weeks of the database), SIM_M_DB for similar months (the months of January 2017 and 2018) and dissimilar months (all months from February to December in the database) and SIM_Y_DB for similar years (2017) and dissimilar years (2016: because it is further back in time, this year is less representative of current situations).

In TRAIT_1, the signals are sorted in order to keep only the signals to be processed. Specifically, nine signals are captured by the sensor CAP so as to have values from three sensors (accelerometer, magnetometer and gyrometer) and in the three Euclidean dimensions. However, it may be that the method does not desire to keep all of the raw data. For example, the method may decide to keep only six values instead of the nine values because the user is, for example, in a recumbent position and does not use the magnetometer. In this case, in TRAIT_1, the three values from the magnetometer are not retained.

Extraction EXTR_Tr_Dt of the raw data is performed in the database MVT_DB so as to retrieve the portion MVT_Tr_Dt of the data in the database which were acquired by the sensor on said given date (reference date referred to as Tr) and for said given duration also referred to as the reference duration Dt. These raw data may be stored in a transitory or non-transitory memory of the sensor or of the device or in a database located in an external equipment, such as a computer or a server for example.

In this exemplary implementation, the motion raw data are collected on Tuesday Feb. 6, 2018 from 10:00 to 11:00. Dt therefore corresponds to a duration of one hour.

In TRAIT_2, processing operations are performed on the collected and segmented signals of interest, representative of the portion MVT_Tr_Dt of the raw data in the database. The processing operations are, in a non-limiting manner, low-pass filtering in order to denoise the information, normalization in order to harmonize the raw data, resampling of data in order to synchronize sources, etc.

In FIG. 1, in P2, the raw data of the database MVT_Tr_Dt acquired in P1 are classified REP in data classes according to a non-supervised classification method, these data classes representing at least one anonymized posture of said person.

Figure 3:
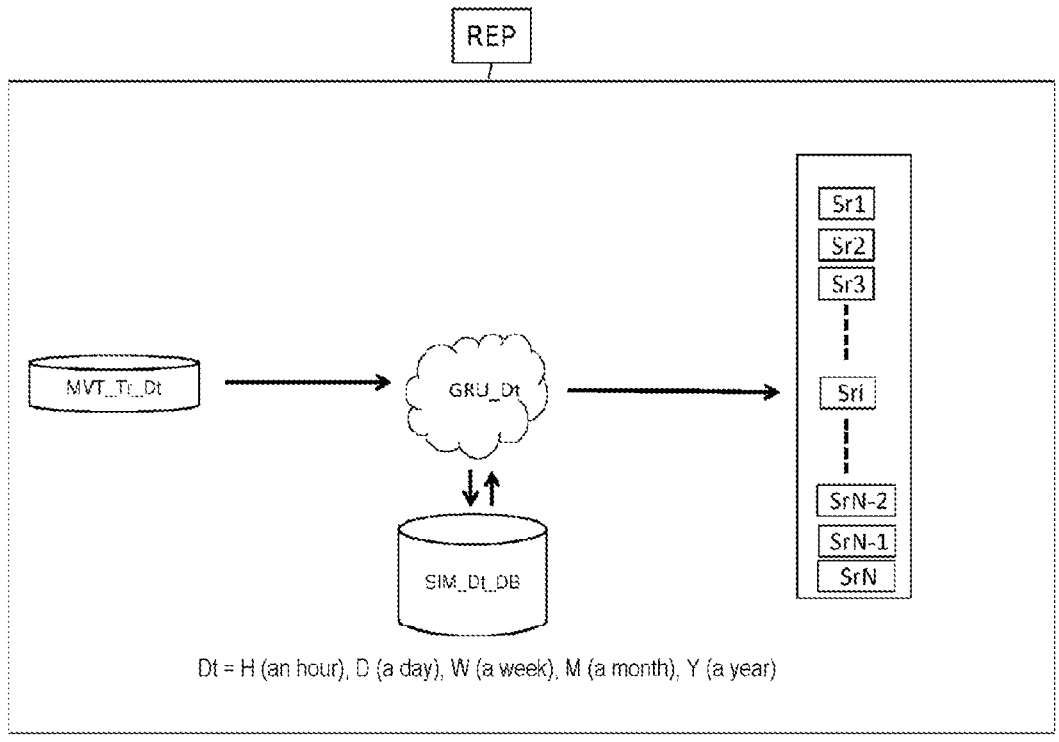
FIG. 3 shows another of the actions performed by the method of FIG. 1 in greater detail.
Figure 4:
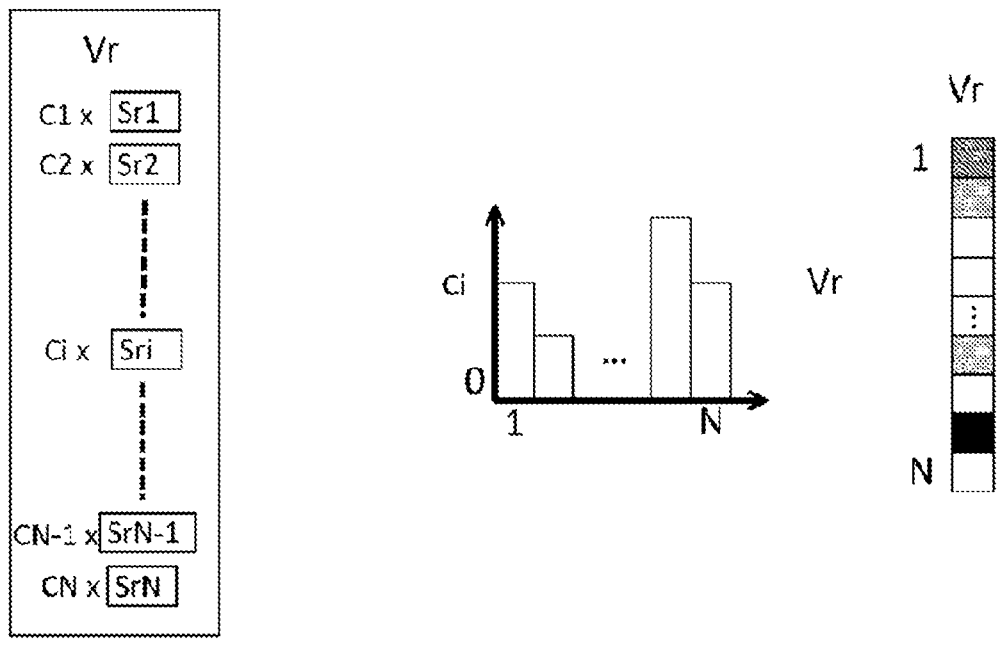
FIGS. 4A, 4B and 4C show various examples of data structures obtained according to the method of FIG. 1.

As shown in FIG. 3, such a classification REP comprises classification of the raw data, stored in the database MVT_Tr_Dt, which represent anonymized similar postures of said person grouped into data classes Sr1, . . . , Sri, . . . , SrN. In this exemplary implementation, the data classes are learned automatically by means of unsupervised clustering of time series on the basis of the knowledge base SIM_Dt_DB.

In order to obtain this classification by anonymized postures of said person, the method uses GRU ("Gated Recurrent Unit") recurrent neural networks learned beforehand using the base SM_Dt_DB. As mentioned in the above paragraph, different data classes Sr1, . . . , Sri, . . . , SrN were determined by clustering using the base SIM_Dt_DB. A learning process follows in order to model a GRU network capable of classifying these motion raw data in data classes representing anonymized postures of said person.

In FIG. 1, in P3, a data structure of the body activity of an individual, for the date Tr and the duration Dt, is calculated CALC_STR.

In one exemplary implementation shown in FIG. 4A, the data structure, denoted by Vr, is a histogram or a vector of data classes Sri recognized in P2. Each value of the histogram represents the number Ci of times a data class Sri has been recognized.

In another exemplary implementation shown in FIG. 4B, the data structure Vr is represented by a histogram of the different data classes and their number for the given duration. The abscissa gives the number N of different data classes and the ordinate gives the number Ci of times a given data class has been identified by the method.

In another exemplary implementation shown in FIG. 4C, the data structure Vr is represented by a stack of square shapes. Each square represents a different data class. For each of the data classes, the number Ci of times that the data class has been identified for the given duration is represented by a number of black pixels within the square.

In FIG. 1, in P4, the data structure Vr is compared COMP with one or more other data structures.

Figure 5:
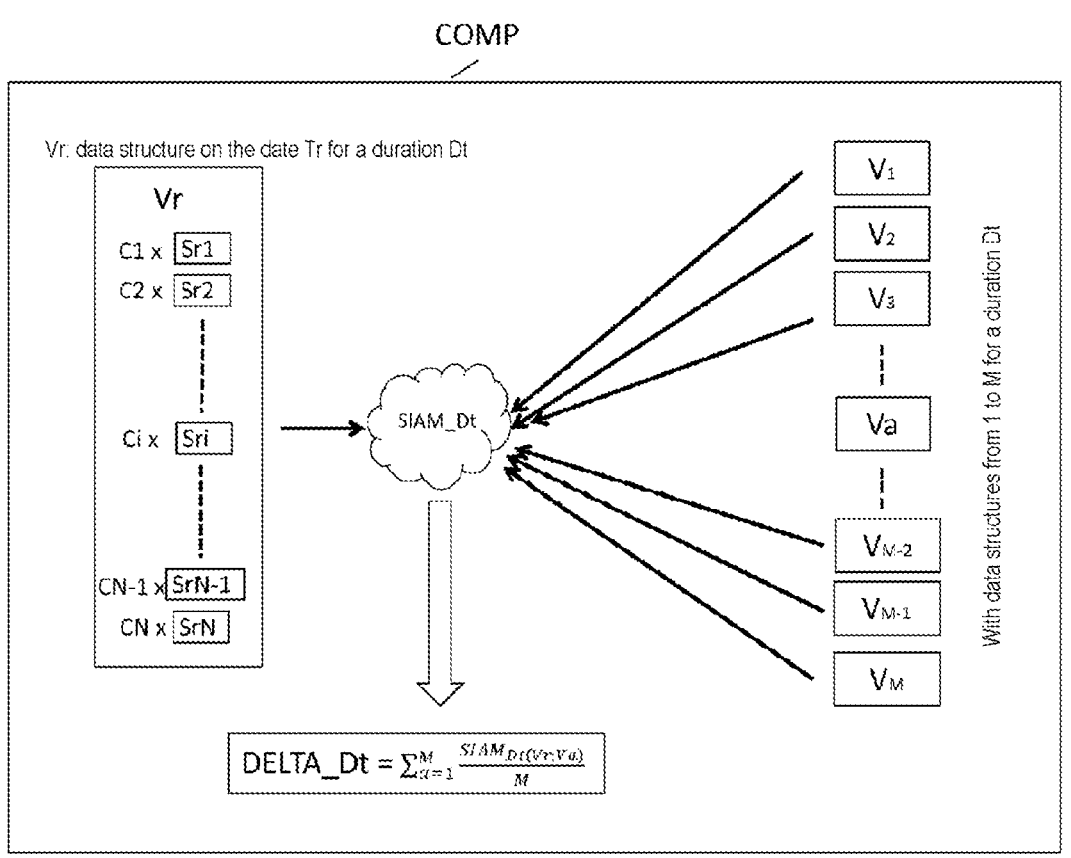
FIG. 5 shows a calculation of variation in body activity performed according to the method of FIG. 1 in greater detail.

To that end, as shown in FIG. 5, the comparison COMP consists of predictions of similarity of the data structure Vr in comparison with other data structures of body activity VI, . . . , Va, . . . , VM calculated for data acquisitions in prior periods (prior dates but for a similar duration). The aim is to know whether the data structure Vr is similar to the other data structures characteristic of its time range (here, in this example, every Monday from 10:00 to 11:00) in the past of the individual or on one or more different dates, but still for the same duration Dt (for example from 11:00 to 12:00 on Monday February 5 of the year before). If the structure Vr is similar to a data structure Va of a prior date a, this indicates that there is no significant change in the body behavior of the individual in view of the comparison between the body activity on the date Tr and the body activity on the date Ta. This comparison is made over a set of prior dates (M dates as illustrated in FIG. 5) with respect to the reference date Tr. A weighted average of all of these comparisons is then calculated in order to obtain a value DELTA_H representative of a first estimate of a value of the autonomy of the user.

Siamese neural networks (SIAM_Dt in FIG. 5) make it possible to make this type of comparison. If two data structures that have been learned by the network show the same body behavior in the period, the Siamese network produces a measurement close to 0. If two data structures are dissimilar (e.g. the body behavior of Tuesday between 10:00 and 11:00 is different from that of Sunday between 22:00 and 23:00), the Siamese network produces a measurement close to 1. Next, to calculate the value DELTA_Dt, a weighted average of the comparison values between the data structure to be evaluated (Vr in the diagram of FIG. 5) and the different data structures already measured on prior dates (Va in the diagram of FIG. 5) is produced.

The aim is to make comparisons with a plurality of prior dates on which the person should engage in similar activities, follow the same routine (for example, Mondays from 10:00 to 11:00). The difficulty is in choosing these prior dates appropriately in order to characterize an abnormal activity and not just a slight difference in habit. This choice of relevance can be made by an expert (physician, auditor) following a preliminary study of the habits of the person to be tracked but also by the method itself if it has sufficient data concerning the habits of the person to be tracked and therefore appropriate comparison times. As an alternative, this choice of relevance can be made both by the expert and by the method.

To obtain a plurality of values of variations in body activities DELTA_Dt, the method uses different models SIAM_Dt learned beforehand. These models are Siamese neural networks which have learned the similarities and dissimilarities over, for example:

databases SIM_H_DB (Dt=H for "Hour") in timeslots of one hour,

SIM_D_DB (Dt=D for "Day") in timeslots of one day,

SIM_W_DB (Dt=W for "week") in timeslots of one week,

SIM_M_DB (Dt=M for "month") in timeslots of one month,

SIM_Y_DB (Dt=Y for "year") in timeslots of one year.

These databases are subsets of data of the database MVT_DB (see FIG. 2). After learning, it is the Siamese neural networks SIAM_Dt with respect to the databases SIM_Dt_DB which measure the similarity between the data structures in order to compare them.

According to another exemplary implementation of the comparison COMP, the comparison COMP consists in calculating the similarity DELTA_D between the preceding day (Monday) and all of the other Mondays in the database MVT_DB. To that end, the reference day in question is the day preceding the given date because all of the data are available for that day. The variations in the behavior of the individual on preceding Mondays are then considered. If no variation is noticed, the body activity of the user is considered to be usual. If one or more variations have been noticed with respect to the preceding Mondays, the body activity of the user is considered to be "deteriorating". In the same way, the method calculates an estimate of the similarity DELTA_W between the preceding week (S5 2018) and the other weeks of the database MVT_DB, and, if the database MVT_DB allows it, calculates the measurements of similarity of weeks, months and years as follows:

an estimate of the similarity DELTA_M between the month corresponding to the date Tr and the months chosen by the method or by a third party because they are similar in terms of monthly activities (for example all of the months of January for each year), an estimate of the similarity DELTA_Y between the year corresponding to the date Tr and the years chosen by the method or by a third party because they are similar in terms of annual activities (the year 2017 in this example).

Figure 6A:
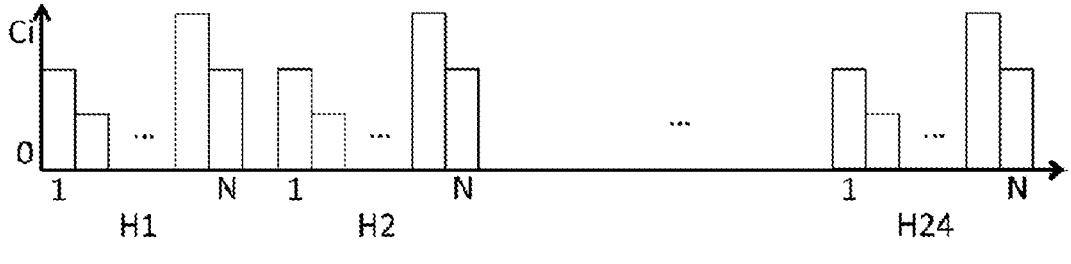
FIGS. 6A and 6B show examples of visualization of data structures over one or more days.

In one exemplary implementation shown in FIG. 6A, the vector characteristic of the body activity of the user over a day is the concatenation of the 24 data class histograms.

Figure 6B:
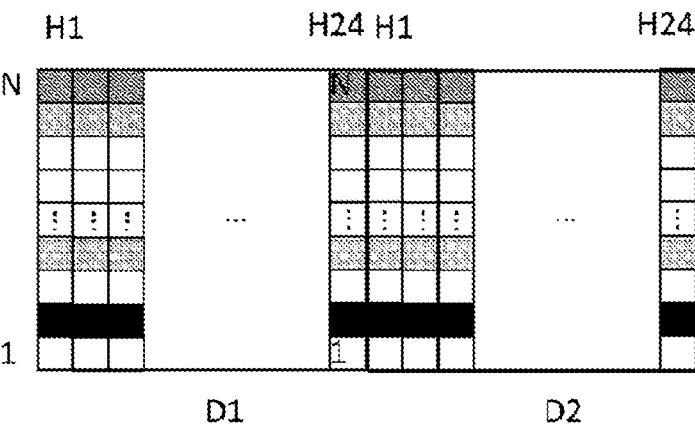

In the exemplary implementation of FIG. 6B, the vector characteristic of the body activity of the user over a day D1, D2, etc. is the concatenation of the 24 columns of N squares representing 24 timeslots, respectively. The squares represent a group of data representing similar motions. Of course, in the same way, such a characteristic vector can be calculated to characterize the body activity of the user over a longer period, such as a week, a month or a year.

In FIG. 1, in P5, the method comprises calculating an autonomy value A according to the similarities predicted in P4 over the different analysis durations produced. In one exemplary implementation, such a calculation uses the following equation:

$$A=WH*\text{DELTA\_}H+WD*\text{DELTA\_}D+ \\ WW*\text{DELTA\_}W+WM*\text{DELTA\_}M+ \\ WY*\text{DELTA\_}Y,$$

with WH, WD, WW, WM, WY being real weighting numbers.

These real weighting numbers are used to give greater importance to one-off changes (for example WH=0.8) than to monthly dissimilarities (for example WM=0.05) and annual dissimilarities (for example WY=0.01). The real weighting numbers may be zero if the knowledge base MVT DB does not allow the calculation, through lack of data, of the corresponding similarities. These weights can be defined manually by an expert (physician, auditor) following an analysis of changes in behaviors of the person to be tracked, or automatically by studying the history of the habits of the tracked person. As an alternative, these weights can be defined both manually and automatically.

In FIG. 1, in P6, the autonomy value A is compared COMP_Z with a value Z.

According to the result of the comparison, in P7, information relating to the calculated variation is generated (GEN).

If the value A is higher than a value Z, then the method activates a service detailed in FIG. 1, in P8. Otherwise, the method acquires new data in P1.

The information generated in P7 represents an interpretation of a value corresponding to the difference between the value A and the value Z. The value A, when communicated by the service described next in P8, makes it possible to give simple and easily understandable information to the appropriate services or to the family regarding the level of autonomy of the user. This information may be textual, graphic or any other means of information.

In FIG. 1, in P8, a communication COM is established in order to inform an individual of the value A.

Such a communication COM can be implemented to inform the individual, their companions, their close friends or family members, medical staff, etc. (if consent is given by the individual) of their change in body habits by transmitting an interpretation of the value A. This communication can consist in sending an email, an SMS text message, a telephone call, a sound or visual alarm or any other means in order to alert a third party.

In FIG. 1, in P9, the change in behavior of the user over a given period is estimated in order to determine whether or not it is necessary to update all of the Siamese neural network models learned beforehand. To that end, the method defines thresholds according to the different durations characterizing each Siamese neural network (hour, day, week, month and year in this example). The calculated values of A based on recent captured activity data are compared with these thresholds as follows:

If, at the end of the current timeslot, the value A is close to 0 (according to a new threshold Tau_H=0.2 for example), then the method can include the data extracted during this timeslot as similar in the database SIM_H_DB;

If, at the end of the day, the value A is close to 0 (according to a new threshold Tau_D=0.1 for example), then the method can include the data extracted over the entire day as similar in the database SIM_D_DB;

If, at the end of the week, the value A is close to 0 (according to a new threshold Tau_W=0.15 for example), then the method can include the data extracted over the entire week as similar in the database SIM_W_DB;

If, at the end of the month, the value A is close to 0 (according to a new threshold Tau_M=0.15 for example), then the method can include the data extracted over the entire month as similar in the database SIM_M_DB;

If, at the end of the year, the value A is close to 0 (according to a new threshold Tau_Y=0.25 for example), then the method can include the data extracted over the entire year as similar in the database SIM_Y_DB.

Otherwise, the method does not add current data to the learning databases SIM_Dt_DB.

In FIG. 1, in P10, the neural network models SIAM_Dt linked, respectively, to the databases SIM_Dt_DB are updated with the new data in order to improve their ability to identify non-routine situations. In particular, if a substantial change is observed in the general behavior of the individual, the models must be heavily modified in order to correspond to the new habits by being fully re-trained using well-known learning algorithms (e.g. fine tuning, transfer learning, adaptive learning, etc.). For example, at the end of the week, the models SIAM_H, SIAM_D, SIAM_W can be re-trained using the new databases SIM_H_DB, SIM_D_DB and SIM_W_DB. At the end of the year, the models SIAM_M, SIAM_Y can be re-trained using the new databases SIM_M_DB and SIM_Y_DB.

Figure 7:
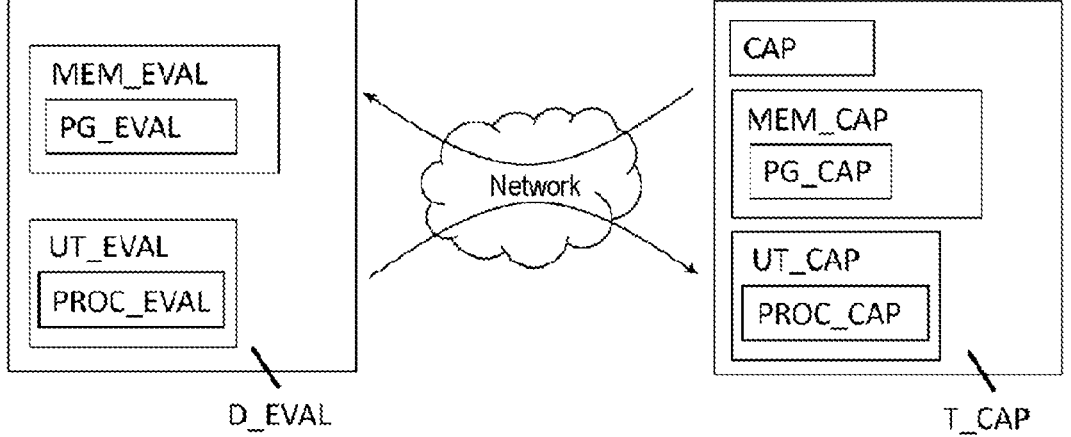
FIG. 7 shows a device for evaluating the body activity of a user implementing the method for evaluating the body activity of a user of FIG. 1.

According to one particular embodiment of the invention shown in FIG. 7, the actions performed by the evaluation method are implemented by a system comprising an evaluation device D_EVAL and a terminal T_CAP for acquiring data.

The evaluation device D_EVAL is for example a computer or a server. To that end, the evaluation device D_EVAL has the conventional architecture of a computer and comprises in particular a memory MEM_EVAL and a processing unit UT_EVAL, which is equipped for example with a processor PROC_EVAL and is controlled by the computer program PG_EVAL stored in the memory MEM_EVAL. The computer program PG_EVAL comprises instructions for implementing the actions of the method for evaluating the body activity of a user as described above, when the program is executed by the processor PROC_EVAL. On initialization, the code instructions of the computer program PG_EVAL are for example loaded into a RAM memory (not shown) before being executed by the processor PROC_E-VAL. The processor PROC_EVAL of the processing unit UT_EVAL implements in particular the actions of the method for evaluating the body activity of a user described above, according to the instructions of the computer program PG_EVAL.

The data acquisition terminal T_CAP is for example a connected object worn/carried by the user. To that end, the acquisition terminal has the conventional architecture of a computer and comprises in particular a memory MEM_CAP and a processing unit UT_CAP, which is equipped for example with a processor PROC_CAP and is controlled by the computer program PG_CAP stored in the memory MEM_CAP. It also comprises a motion sensor CAP allowing all sorts of motion data (for example: accelerometric, gyroscopic, magnetometric) to be captured. The computer program PG_CAP comprises instructions for implementing the actions of the method for evaluating the body activity of a user as described above, when the program is executed by the processor PROC_CAP. On initialization, the code instructions of the computer program PG_CAP are for example loaded into a RAM memory (not shown) before being executed by the processor PROC_CAP. The processor PROC_CAP of the processing unit UT_CAP implements in particular the actions of the method for evaluating the body activity of a user described above, according to the instructions of the computer program PG_CAP.

Regarding step P1, in conjunction with FIG. 2, as already explained above, the process TRAIT_1 makes it possible to obtain and select signals of interest to be processed. The process TRAIT_1 may be performed by the terminal T_CAP as follows:

the motion data acquired by the sensor CAP are stored in the memory MEM_CAP in real time and processed by the process TRAIT_1. The processed data are then transmitted to the memory MEM_EVAL in order to be finally stored in the database MVT_DB.

The process TRAIT_1 may also be performed afterward, that is to say the acquisition data not processed by the terminal T_CAP are stored directly in the database MVT_DB and processed afterward with the process TRAIT_1 by the evaluation device D_EVAL (see FIG. 2, the dashed arrows between TRAIT_1 and MVT_DB). The process TRAIT_1 may also be a combination of processing operations performed in real time in the memories MEM_CAP and MEM_EVAL, the processed data being stored afterward in the database MVT_DB in order to adapt to the storage and computing performance of the terminal T_CAP.

Depending on the embodiment, the evaluation device D_EVAL and the terminal T_CAP may be interconnected and exchange data over one or more communication links, using one or more networks of different types (a network in FIG. 7) and different protocols. Examples of networks are a fixed network, a cellular network (for example according to 2G (GSM, GPRS, EDGE), 3G (UMTS), 4G (LTE), LTE-A, LTE-M, WCDMA, CDMA2000, HSPA or 5G standards, or their variants or evolutions), another type of radio network (e.g. Wi-Fi® or Bluetooth®), an IP network, a combination of a plurality of these networks, etc. For this, the evaluation device D_EVAL and the terminal T_CAP will be configured with suitable data communication means.

From step P2 of FIG. 1, all of the calculations performed to implement the evaluation method can be performed just by the evaluation device D_EVAL. In this embodiment, the terminal T_CAP only retransmits the measurement data to the device D_EVAL. The memory MEM EVAL may include one or all of the databases (MVT_DB, MVT_Tr_Dt, SIM_Dt_DB) of the method, but this is not obligatory. Indeed, these databases may be distinct from the device D_EVAL. As a variant, for more flexibility, one or more of these databases is distinct from the device D_EVAL, while the other databases of the set will be included in the device D_EVAL.

To generalize the various calculation possibilities of the steps of the evaluation method, and according, respectively, to various particular embodiments of the invention not represented schematically, each calculation step of the method may be carried out, respectively, by the device D_EVAL or the terminal T_CAP so as to represent all of the possible combinations of calculation configurations between the device D_EVAL and the terminal T_CAP.

Needless to say, the embodiments described above have been given purely by way of entirely non-limiting illustration, and numerous modifications may be easily made by a person skilled in the art without departing from the scope of the invention.

The invention claimed is:

1. A method for evaluating a body activity of a user, implemented by a computing device, wherein the method comprises:

during a first performance of the body activity on a first date and for a duration, acquiring raw data on motion of said user from a motion sensor;

classifying said raw data in at least one data class, according to at least one non-supervised classification method;

on the basis of said at least one data class, calculating a first data structure representative of the first performance of the body activity;

comparing said first data structure with at least one second data structure, each second data structure representative of a prior performance of the body activity for said duration by said user prior to the first date;

as a result of said comparison, evaluating a variation between the first performance of the body activity and the at least one prior performance of the body activity; and calculating an autonomy value according to a plurality of variation evaluations calculated for a plurality of different timeslots of different durations, the variation evaluations including a comparison of the body activity in a timeslot with prior body activities corresponding to the same timeslot, said autonomy value being obtained by adding the plurality of variation evaluations, a weighting coefficient being assigned to each of said variation evaluations respectively.

2. The method as claimed in claim 1, wherein said duration is determined with respect to the obtaining of a desired minimum number of different data classes, into which to distribute the acquired motion raw data.

3. The method according to claim 1, comprising: comparing the autonomy value with a certain value, and depending on a result of the comparison, generating information relating to the calculated variation.

4. The method as claimed in claim 3, wherein the generated information is communicated to a person authorized by said user.

5. An evaluation device for evaluating a body activity of a user, said evaluation device comprising:

a processor configured to implement a method comprising:

during a first performance of the body activity on a first
date and for a duration, acquiring raw data on motion
of said user from a motion sensor;

classifying said raw data in at least one data class,
according to at least one non-supervised classification method;

on the basis of said at least one data class, calculating
a first data structure representative of the first per-
formance of the body activity;

comparing said first data structure with at least one
second data structure, each second data structure
representative of a prior performance of the body
activity by said user prior to the first;

as a result of said comparison, evaluating a variation
between the first performance of the body activity
and the at least one prior performance of the body
activity; and calculating an autonomy value according to a plurality
of variation evaluations calculated for a plurality of
different timeslots of different durations, the variation evaluations including a comparison of the body
activity in a timeslot with prior body activities cor-
responding to the same timeslot, said autonomy
value being obtained by adding the plurality of
variation evaluations, a weighting coefficient being
assigned to each of said variation evaluations respec-
tively.

6. A non-transitory computer-readable storage medium,
comprising instructions of a computer program stored
thereon which when executed by a processor of an evaluation device configure the evaluation device to perform a
method for evaluating a body activity of a user comprising:

during a first performance of the body activity on a first
date and for a duration, acquiring raw data on motion
of said user from a motion sensor;

classifying said raw data in at least one data class,
according to at least one non-supervised classification
method;

on the basis of said at least one data class, calculating a
first data structure representative of the first perfor-
mance of the body activity;

comparing said first data structure with at least one second
data structure, each second data structure representative
of a prior performance of the body activity for said
duration by the user prior to the first date;

as a result of said comparison, evaluating a variation
between the first performance of the body activity and
the at least one prior performance of the body activity;
and calculating an autonomy value according to a plurality of
variation evaluations calculated for a plurality of dif-
ferent timeslots of different durations, the variation
evaluations including a comparison of the body activity
in a timeslot with prior body activities corresponding to
the same timeslot, said autonomy value being obtained
by adding the plurality of variation evaluations, a
weighting coefficient being assigned to each of said
variation evaluations respectively.

* * * * *